United States Patent
Calvo (12)

(10) Patent No.: US 6,277,575 B1
(45) Date of Patent: Aug. 21, 2001

(54) PROCESS AIMED AT EVIDENCING THE STATE OF A MALIGNANT CELL

(76) Inventor: Fabien Calvo, 46 rue des Archives, 75004 Paris (FR)

( * ) Notice: Subject to any disclaimer, the term of this patent is extended or adjusted under 35 U.S.C. 154(b) by 0 days.

(21) Appl. No.: 09/297,069
(22) PCT Filed: Oct. 31, 1997
(86) PCT No.: PCT/FR97/01960
 § 371 Date: Jul. 6, 1999
 § 102(e) Date: Jul. 6, 1999
(87) PCT Pub. No.: WO98/18960
 PCT Pub. Date: May 7, 1998

(30) Foreign Application Priority Data

Oct. 31, 1996 (FR) .................................................. 96 13326

(51) Int. Cl.[7] .............................. C12Q 1/68; C12N 1/38; C12N 5/08; C07H 21/04
(52) U.S. Cl. ............................ 435/6; 435/244; 435/366; 435/375; 435/377; 536/24.3; 536/24.31; 536/24.33
(58) Field of Search .................... 435/6, 252.3; 536/23.1, 536/24.31, 24.3, 24.33; 436/244

(56) References Cited

U.S. PATENT DOCUMENTS

| | | | |
|---|---|---|---|
| 5,264,343 | 11/1993 | Krystosek et al. | ........................ 435/6 |
| 5,707,808 | * 1/1998 | Roslaniec et al. | ........................ 435/6 |
| 5,719,023 | * 2/1998 | Zarling et al. | ............................ 435/6 |
| 5,817,462 | * 10/1998 | Garini et al. | .............................. 435/6 |

FOREIGN PATENT DOCUMENTS

| | | |
|---|---|---|
| 0 500 290 | 8/1992 | (EP) . |
| 94/19492 | 9/1994 | (WO) . |
| 95/09928 | 4/1995 | (WO) . |
| 95/13375 | 5/1995 | (WO) . |
| 96/25507 | 8/1996 | (WO) . |

OTHER PUBLICATIONS

Hopman et al. "In situ hybridization as a tool to study numerical chromosome aberrations in solid bladder tumors" Histochemistry, 1988, 89:307–316.*

Pinkel et al. Proc. Nat. Acad. Sci. USA "Cytogenetic analysis using quantitative, high sensitivity fluorescence hybridization" 1986, 83:2934–2938.*

Cremer et al. "Role Of Chromosome Territories In The Functional Compartmentalization Of The Cell Nucleus", *Cold Spring Harbor Laboratory Press*, pp. 777–792, (1993).

A.K. Csink et al., "Genetic modification of heterochromatic association and nuclear organization in Drosophila", Nature vol. 381, Jun. 1996, pp. 529–531.

A.F. Bernburg et al., "Perturbation of Nuclear Architecture by Long–Distance Chromosome Interactions", Cell, vol. 85, May 1996, pp. 745–759.

R. Foisner et al., "Integral Membrane Proteins of the Nuclear Envelope Interact with Lamins and Chromosomes, and Binding is Modulated by Mitotic Phosphorylaton", Cell, vol. 73, Jul. 1993, pp. 1267–1279.

(List continued on next page.)

Primary Examiner—Stephanie W. Zitomer
Assistant Examiner—B J Forman
(74) *Attorney, Agent, or Firm*—Foley & Lardner (57) ABSTRACT

The malignant or otherwise diseased state of a cell can be determined in tissues fixed by techniques such as the formalin and parafin methods. This determination is made by (1) studying the precise conformation (i.e. position and structure) of at least one gene within a chromosome of a targeted cell and (2) measuring the deviation of gene conformation in comparison to a non-diseased cell. Accordingly, methods for evaluating the malignancy index of cells, as well as monitoring the effectiveness of therapeutic treatment, are provided.

3 Claims, 4 Drawing Sheets

OTHER PUBLICATIONS

M.M. Haag et al., "Reverse Transformation and Genome Exposure in the C6 Glial Tumor Cell Line", Cancer Investigation, 12(1), 1994, pp. 33–45.

R. Hulspas et al., "The nuclear position of pericentromeric DNA . . . human lymphocytes", Chromosoma, vol. 103, 1994, pp. 286–292.

K. Klinger et al., "Rapid Detection of Chromosome Aneuploidies . . . In Situ Hybridization (FISH)", Am. J. Hum. Genet. vol. 51, 1992, pp. 55–65.

Laura Manuelidis, "A view of interphase chromosomes", Science, vol. 250, Dec. 1990, pp. 1533–1540.

R. Nagele et al., "Precise Spatial Positioning of Chromosomes During Prometaphase: Evidence for Chromosomal Order", Science, vol. 270, Dec. 1995, pp. 1831–1835.

M. Nemani et al., "Activation of the human homologue of the *Drosophila sina* gene in apoptosis and tumor suppression", Proc. Natl. Acad. Sci., vol. 93, Aug. 1996, pp. 9039–9042.

T. Waldman et al., "Uncoupling of S phase and mitosis induced by anticancer agents in cells lacking p21", Nature, vol. 381, Jun. 1996, pp. 713–716.

\* cited by examiner

PROCESS AIMED AT EVIDENCING THE STATE OF A MALIGNANT CELL

This application is a 371 of PCT/FR97/01960 filed Oct. 31, 1997.

The present invention relates, in general, to the determining of a reorganization of the nucleus during tumor suppression and the consequences resulting therefrom both at the diagnostic and at the therapeutic, in particular anticancer therapy, level.

An increasing number of signs suggest that the regulation of the expression of genes, whether regarding their activation or their silencing, occurs in two stages in which a compartmentalization of the chromosomes in the nucleus before transcription is first of all observed.

The present invention has demonstrated the fact that, in cancerous tissues, this compartmentalization occurred differently compared with a normal cell, which could constitute a diagnostic tool.

It has been possible to carry out this observation in particular by studying the mechanism of the p21WAF1 gene and its behavior during the activation which contributes to the suppression of the tumorigenic process.

It has been possible for this phenomenon to be demonstrated in particular by means of an improvement in the DNase I method which made it possible to monitor this process.

The DNase I method is based on the observation that the chromatin active in transcription is more particularly sensitive to the action of nucleases. It contains, in particular, sites which are hypersensitive to DNase I (these are relatively short DNA segments which are very sensitive to a large number of cleaving agents). These nucleosome-free DNA segments are associated with various functions in the expression of the gene. Such "open chromatin regions" may allow the binding of specific factors and possess major regulatory functions; it is said in this case that the labeled DNA is the exposed DNA.

It has therefore been possible to study, by means of this method, the possible relationships between the transcription of genes and their hypersensitivity to DNase I in situ, especially as a marker allowing analysis of the organization of the overall genome in cancer phenomena.

The general method which will be called hereinafter "DNase method" is described in particular in published American Patent U.S. Pat. No. 5,264,343, this document is cited here by way of explicit reference and the information which it contains will not be repeated in greater detail. Reference may also be made to the publication by Puck et al. (Puck T. T., Bartholdi M., Krystosek A., Johnson R. and M. Haag. Somatic Cell and Molec. Genetics 17, 489–503, 1991).

However, the method described in the patent in question does not allow analysis of tissues fixed by the formalin and paraffin method, that is to say tissues obtained by the method used in most anatomical pathology laboratories. Indeed, the method described in the American patent relates essentially to the analysis of systems in cell culture.

One of the objectives of the present invention is therefore to provide a new DNase method which makes it possible to carry out diagnoses on fixed tissues.

However, the subject of the present invention is furthermore, in general, methods intended to determine the state of a malignant cell in which the precise conformation of at least one gene within the nucleus of said cell is determined by labeling said gene in situ and evaluating the deviation of this conformation in relation to a normal cell as an index of its malignancy.

Indeed, while the determination of the position of the exposed DNA by the DNase method allows overall analysis of the state of malignancy of a tissue, on the other hand, the study of the precise conformation of at least one gene within a chromosome and the measurement of its deviation from the normal allows not only a classification of the various types of malignant cells, but also an evaluation of their malignancy index and of course, thereby, the monitoring of a therapeutic treatment.

It should be recalled that in the text which follows, the term "malignant" or "malignancy index" will also be optionally used to describe phenomena not directly linked to oncogenesis but also characterized by a disorganization of the chromosomes within the nucleus, for example cystic fibrosis.

This second method is based, here again, on the demonstration of the fact that by evaluating the conformation, that is to say both the position but also, if necessary, the structure of one or more genes by any appropriate technique, in particular by fluorescence in situ hybridization for example (FISH), it is observed that, depending on the malignant state of the cell, some genes involved in tumor suppression and/or activation move from the center of the nucleus outward and that their deviation from the normal constitutes a good sign of the state of the cell which is called hereinafter "malignancy index", it being possible for this index to be evaluated by any appropriate method between a normal cell and a cell whose malignancy will be considered as irreversible.

This method allows a classification of tumors according to the position of the various genes in the nucleus and even of the three-dimensional structure of these specific genes in the nucleus.

In the first instance, it will be possible to study the position of the genes in the nucleus simply by studying the position of the centromers of a chromosome carrying them.

This method may be used with hybridization probes of the centromeric probe type; in this case, the normal corresponds to a peripheral location of the chromosomes carrying the centromeric probes and, in particular, as will be developed hereinafter, these centromeric probes may correspond to chromosomes 13q and 16q, which are carriers of HUMSIAH and Rbr-2 genes colocated on chromosome 16q and the Rb gene located on chromosome 13q, these genes being involved in the phenomenon of cancer suppression. It is understood that the centromeric probes which can be used in the methods according to the invention may correspond to any other cellular chromosome, in the same way that the gene labeling, according to the methods of the invention, may correspond to one or more genes carried on one or more chromosomes chosen from all of the chromosomes in the cell.

However, as has been indicated, the present invention also relates to a method intended to determine the overall state of malignancy of the cells of a tissue after fixing, characterized in that the exposed nuclear DNA is labeled and the entire DNA is labeled with a marker specific for the DNA, these two markers being capable of emitting uncontaminated specific signals.

"Uncontaminated specific signals" is understood to mean that it is possible to visualize separately, without notable contamination, the two signals corresponding to the two markers.

In general, the exposed nuclear DNA is labeled by the DNase I method, as was described above, and the DNA is labeled with the specific marker chromomycin A-3 (CA-3).

Among the exposed nuclear DNA markers, there should be mentioned more particularly tetramethylrhodamine used in combination with peroxidase. The labeling with peroxidase may be carried out by any appropriate method, in particular couplings of the avidin or streptovidin/biotin or DIG/antiDIG (DIG for digoxigenin) type.

Indeed, the peroxidase substrate, called tyramide-TRITC, makes it possible to amplify the signal obtained by a factor of 15 and thus makes it possible to analyze a fine distribution of the signal inside the nucleus.

The importance of using a marker specific for DNA is that it makes it possible to analyze the cell cycle in a semiautomatic manner, and therefore to make a correlation between the exposure of the genome obtained by means of the DNase I method and the cell cycle phases.

Thus, the present invention also relates to a method according to the invention, characterized in that the position of the exposed nuclear DNA relative to the cell cycle phase determined is evaluated by the marker specific for DNA as an index of the state of malignancy of the tissue cells.

In addition, the two fluorochromes thus used have an emission in the same region of the light spectrum, that is to say 600 nm, but their specific excitation is very different, 467 nm for CA-3 and 514 nm for TRITC, as well as the extinction coefficients, which makes it possible to obtain specific signals without any contamination between the two markers. In addition, by means of these markers, the analysis can be carried out with a single argon laser which is the most widespread laser in microscopy.

This method according to the present invention makes it possible to use tissues fixed in formalin according to routine methods and thus allows analysis of tissues obtained, for example, from a tissue collection.

In general, the methods thus described make it possible to diagnose malignant states from tissues and/or cell cultures and allow, by means of the established classification, a prognosis factor in diagnostic pathology.

In particular, they make it possible to differentiate, for example, between simple hyperplasias (breast, prostate) which are benign pathologies, atypical hyperplasias (breast, prostate) exhibiting a variable evolution which is difficult to establish and which constitute pathologies known to be "borderline", but which, in the present case, can be more easily classified by means of the various labeling components which have been mentioned, and the carcinoma in situ.

These methods also allow the introduction of rapid models allowing anticancer products to be tested, and in particular, by studying their action on the reorganization of certain specific chromosomes, a finer classification of the activity of the various agents in question.

Preferably, the methods described above, in which the state of a malignant cell is determined, are used in order to test anticancer products or related products, and then said cell is treated with an anti-cancer product or a related product and the activity of said compound is evaluated by measuring the variation in the malignancy index.

The invention comprises anticancer products or related products, characterized in that they are selected by a method according to the invention.

Related products is understood to designate products acting in pathologies not directly linked to oncogenesis and as defined above.

Of course by the same token, these methods will allow therapeutic monitoring in the event of a treatment.

Finally, the present invention relates to a method for treating cells exhibiting disorganization in the nucleus and the application of this method in the treatment of certain pathologies, in particular tumor pathologies.

The present invention is indeed based on the demonstration of the properties of reorganization of the nucleus associated with the p21WAF1 gene.

The association of p21WAF1 with the p53 signal, its role as inhibitor of cycline-dependent kinases (CDKs) and in the control of chromosomal endoreplication indicate that this gene plays a major role in the control of cell growth.

It has now been demonstrated that the re-expression of p21WAF1 in a model led to a suppression of the tumor.

Accordingly, the present invention relates to a method of treating cells exhibiting disorganization of the nucleus, characterized in that the expression of the product of the p21WAF1 gene or of an equivalent product is brought about or alternatively the product of the gene or the equivalent product is introduced.

The p21WAF1 gene is known and has already been described many times; reference may be made, for its characterization, its isolation or some of its properties, to the documents below and to their references:

Weinberg R. A. Science 254, 1138–1146 (1992)

Telerman A. et al. Proc. Natl. Acad. Sci. USA 90, 8702–8706 (1993)

Amson R. B. et al. Proc. Natl. Acad. Sci. USA 93, 3953–3957 (1996)

Nemani M. et al. Proc. Natl. Acad. Sci. USA 93, 9039–9042 (1996)

El-Deiry W. S. et al. Cell 75, 817–825 (1993)

Harper J. W., Adami G. R., Wei N., Keyomarsi K. & Elledge S. J. Cell 75, 805–816 (1993)

Waga S., Hannon G. J., Beach D. & Stillman B. Nature 369, 574–578 (1994)

Yang Z. Y., Perkins N. D., Ohno T., Nabel E. G. & Nabel G. J. Nature Medicine 1, 1052–1056 (1995)

Xiong Y. et al., Nature 366, 701–704 (1993)

Waldman T., Lengauer C., K. W., K & Vogelstein B. Nature 381, 713–716 (1996).

As will be explicitly stated below, the disorganization of the nucleus may be of tumor origin, but it may involve disorganizations of another type. The methods of treating cells according to the invention, characterized in that the disorganization of the nucleus is due to a tumor or nontumor phenomenon, also form part of the invention.

"Disorganization of the nucleus" is understood to mean a nucleus in which the genetic material, in particular the chromosomes, occupies a place different from that which it occupies in the nucleus of the cell in the normal state, which disorganization may in particular be demonstrated by the methods described above.

Although the phenomenon of disorganization of the nucleus has been more particularly demonstrated in tumor phenomena, this disorganization may also occur in other nontumor type phenomena such as cystic fibrosis (CFTR).

The method according to the present invention thus makes it possible, either through reinduction of the expression of the corresponding p21WAF1 gene, or through the use of a product of the gene or of an equivalent product, that is to say having the same reorganization activity as the product of the p21WAF1 gene, to reorganize the genetic material in the nucleus.

Of course, the induction of the expression of the gene may be replaced by a blocking of the repression of the same gene or of a product of expression.

The expression of the p21WAF1 gene or of an equivalent product may be carried out by any known method, in the examples, in particular, there may be used an expression vector of viral origin into which there has been introduced the corresponding gene under the control of a promoter which is expressed in the cells, this introduction, whether the vector remains nonchromosomal or whether it becomes integrated into the chromosomes, leads to the expression of the product of p21WAF1 and to the reduction in the malignancy of the cells. Among the viral vectors, there should be mentioned, in particular, the adenovirus, retrovirus or herpesvirus vectors or even systems of the synthetic type or even naked DNAs.

Although it is possible to express the p21WAF1 gene in its entirety, some truncated, deleted or mutated versions may exhibit equivalent properties and may therefore also form part of the method according to the present invention.

Of course, it is possible to use the products of the p21WAF1 gene obtained, for example, by cell culture, as well as cultures producing, as previously stated, equivalent products.

It is also possible to envisage an in situ reactivation of the natural p21WAF1 promoter, or alternatively the blocking of the systems for repressing its expression in situ.

In general, the present invention relates to the use of the product of expression of the p21WAF1 gene or of an equivalent product or alternatively of a compound ensuring the expression of said product for the production of a medicament intended to bring about the reorganization of the cell nucleus of cells in cancer processes or processes of the noncancer type with disorganization of the nucleus, as well as a therapeutic composition characterized in that it contains, as active ingredient, the product of expression of the p21WAF1 gene or an equivalent product or alternatively a compound bringing about the expression of said product.

Other characteristics and advantages of the present invention will emerge on reading the examples below which will be described with reference to the accompanying figures whose legends are described below:

FIG. 1:

FIG. 3: Repositioning of chromosome 16 in p21WAF1 U937 transfected cells. [lacuna] and b): fluorescence in situ hybridization (FISH) using an alphoid centromeric probe of chromosome 16, the 2 or 3 points (normally in red), appearing inside the nucleus (normally in blue), represent the fluorescence signals corresponding to the labeled centromeric probe. a) corresponds to the nuclei of control transfected U937 cells (pRSV) and b) corresponds to the nuclei of transfected p21WAF1 U937 cells (p21-WAF1). The nucleus of the control transfected U937 cells and the transfected p21-WAF1 cells are labeled with DAPI (blue). The FISH signal is revealed by tyramide-TRITC (red). Three spots are visible here taking into account a trisomy 16 of the sample.

c) Enlargement of a transfected p21WAF1 U937 cell (p21-WAF1), with the image of the distance code of the nucleus.

d) Representation of the successive layers of the size of a pixel, classified by their distance relative to the border of the nucleus.

e): Reconstruction of a nucleus volume from an image in two dimensions. The sphere (R: radius) was cut into a set of cylinders (radius: $r_i$, height: $h_i$, thickness: $\Delta R$).

f): The peripheral distribution was modeled by random distribution in a crown of thickness 2/10 R.

g): The modeling of distribution of a signal in the crowns of different thicknesses according to the distance with the nuclear border.

a: distribution of random points in a sphere.

b–f: distribution of FISH signals as measured from the border of the nucleus for chromosome 16(b), chromosomes 13/21(c), chromosome 17(d), the p53 gene (e) and the Rb gene (f), respectively.

EXAMPLE 1

Transfection

The complete cDNA encoding the human p21WAF1 gene was cloned into the EcoRI site of the phagemid pBK-RSV (Stratagene). The constructs were transfected using the Lipofectin reagent (Gibco-BRL). $3.5 \times 10^6$ cells are incubated for 8 hours with a Lipofectin (30 µg)-DNA (20 µg) complex.

Northern Blot Analysis

The extraction of mRNA and the Northern blot analyses are carried out using the standard procedure, the p21WAF1 probe corresponds to a cDNA of 2.1 kb. For HUMSIAH, a cDNA fragment of 1.4 kb is used, the Rb1 probe is HP126 (Medgene) and the Rbr-2 probe is a PCR fragment of 393 bp obtained with the following primers:

5'-TGGGACAGCTACCGCAGCATGAGCGA-3' (SEQ ID NO:1) and 5'-CACAGTACAGGGCTGTCGCCGCTGTT-3' (SEQ ID NO:2).

Analysis of Tumorigenicity

The injection of scid/scid mice was carried out as described above (Telerman et al., 1993). $10^7$ cells are injected per site. The animals are monitored for three months. The Mann-Whitney test was carried out for the statistical analysis.

Exposure of the Genome to DNase I

The test of exposure of the genome to DNase I was modified compared with that described by Puck (Puck et al., 1991). The cells are fixed in 4% paraformaldehyde/dehydrated PBS (PBS: phosphate-buffered saline) and stored at −80° C. The in situ nick translation (NT) was carried out using 30 U of DNase I (Boehringer Mannheim, Germany) in an NT buffer (50 mM Tris-HCl, pH 8, 5 mM $MgCl_2$, 10 mM β-mercaptoethanol, 50 ng/ml BSA (bovine serum albumin)) at room temperature and 40 U of DNA polymerase I (Boehringer Mannheim, Germany), 100 mM dNTP labeled digoxigenin mix (Boehringer Mannheim, Germany). The in situ repaired DNA was revealed using anti-digoxigenin antibodies conjugated with peroxidase (Boehringer Mannheim, Germany) and tyramide-TRITC (Du Pont NEN, United States) as substrate. The sections were labeled with chromomycin A3 (Sigma, United States). The analysis was carried out by cofocal scanning laser microscopy (MRC 600 Bio-rad, Great Britain) in fluorescence mode.

Fluorescence in situ Hybridization (FISH)

The FISH was carried out as previously described by Linares-Cruz et al., (Linares-Cruz et al., 1995, Histochemical journal, 27, 15–23). The following probes were used (ONCOR, United States): an alphoid centromeric probe corresponding to chromosome 16 (D16Z2), an alphoid centromeric probe corresponding to chromosome 17 (D17Z1), and alphoid centromeric probes corresponding to chromosomes 13/21 (D13Z1/D21Z1), to the p53 and Rb genes. The analysis was carried out by epifluorescence microscopy (with a cooled 3CCD camera, equipped with a triple passing band, Lhesa France), using numeric narrow aperture lenses (N.A.) (40×; 0.75 N.A.), made digital in a matrix of 768×512 pixels. Each pixel corresponds to 55×55 nm of the object.

Image Analysis

The measurements of distance were carried out using a SAMBA IPS image analysis system (UNILOG, France). The markers were extracted by "top hat" transformation and the nuclei were fractionated by threshold from the image by fluorescence using DAPI. Two binary images were obtained respectively for the markers and the nuclei. Successive erosion was used to measure the distance between the markers and the border of the nucleus. The positions of the markers were determined by the intersection of their image with the distance. This method makes it possible to analyze the entire nuclei independently of their shape. To compensate for the differences in nuclear size, the distances were systematically normalized by dividing each distance value by the radius of the corresponding nucleus.

Model of Distribution of the Distances

The model curves used for comparing the distances obtained experimentally were produced by stereological simulation. The three-dimensional representation of the nuclei is assimilated to a spherical model formed by a cylinder set. The volume of an elementary cylinder ($v_i$) is correlated with the probability ($P_i$) of the presence of markers by: $P_i = v_i / \Sigma v_i$. If R is the radius of the nucleus, $r_i$ the radius of the cylinder, $\Delta R$ the thickness of the cylinder and $h_i$ its height:

$$v_i = \pi \Delta R (2 r_i - \Delta R) h_i.$$

This equation makes it possible to trace the random distribution in a sphere and the peripheral distribution in the crowns of different thickness. With this model, the function obtained is independent of the elliptical shape of the nucleus. The FISH spots adjusted to the focal setting (equatorial plane) are analyzed. More than 100 nuclei were evaluated per case.

Statistical Analysis

The radius of the nucleus is divided into eight classes. Each distance measured between the nuclear border and the FISH signals was recorded in one of these eight classes. The $\chi^2$ test was used to confirm two hypotheses. First, that the distances measured in the p21WAF1 U937 cells are distributed in a similar manner as those measured in the U937 cells transfected with the vector alone. Secondly, that the distances measured in the two cell lines are distributed in a similar manner as the random points in a sphere. $P<0.001$ is considered to indicate a significant difference.

Re-expression of p21WAF1 in a Model System

The transformed cells are the cells of a tumor cell line U937, a tumorigenic line both in vitro and in vivo, which practically does not express p21WAF1, both at the mRNA level and the protein level (Telerman et al., 1993, and Nemani et al., 1996).

It is observed that the daughter cells US3–US4 derived from the U937 tumor cell line, selected by means of the H-1 parvovirus, exhibit a tumor phenotype suppression. It has been shown, for example, that the U937 cells form tumors at 80% of the sites of injection into scid/scid mice whereas the US3 cells do not form any tumor and the U4 cells form one tumor per 20 injection sites. These US3 and US4 cells constitutively express, on the other hand, very high levels of p21WAF1 independently of the p53 route.

Accordingly, these observations led to the study of the effect of p21WAF1 on specific gene expression and the tumor suppression of U937 cells stably transfected with p21WAF1.

Figure 1:
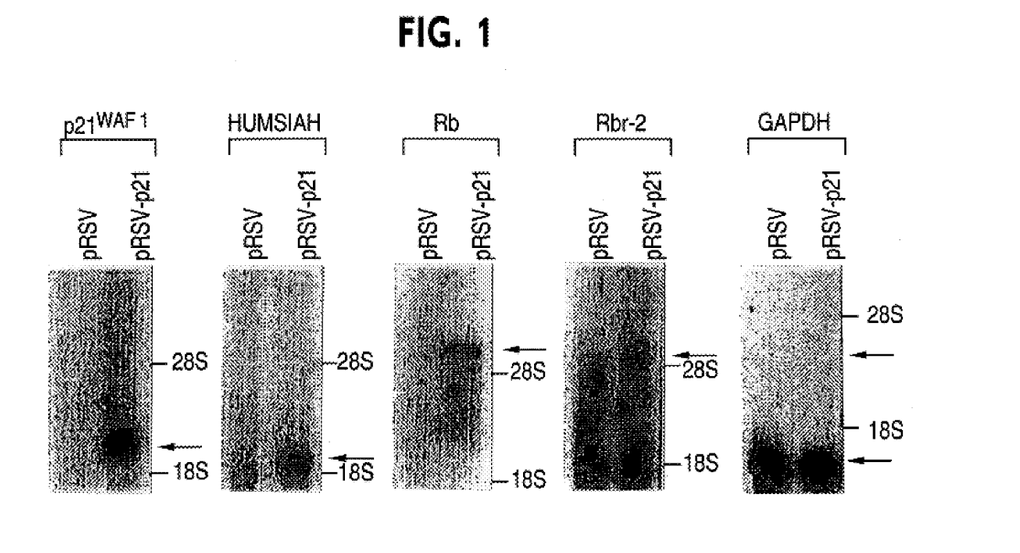
FIG. 1 represents the differential expression of mRNA in transfected U937 cells control (pRSV) and expressing p21WAF1 (pRSV-p21). Northern blot analysis indicates the activation of p21WAF1, HUMSIAH, Rb and Rbr-2 in transfected pRSV-p21 cells compared with the control pRSV cells transfected with the vector alone. GAPDH is used as control probe.

Induction by p21WAF1 of Specific Gene Expression and Suppression of Tumorigenicity After transfection of the U937 cells with the preceding vectors, it is observed, after Northern blot analysis (cf. FIG. 1), that the U937 cells transfected with p21WAF1 (pRSV-p21) have a very high level of mRNA corresponding to the expression of the p21WAF1 gene of the human homolog of the Drosophila "seven in absentia" gene (HUMSIAH). This gene (also called TSAP 3, tumor suppresser activated pathway 3) is activated by the wild-type p53 protein at a very early stage of apoptosis and of the tumor suppression (Nemani et al., 1996 and Amson et al., 1996). In addition, the gene for susceptibility to retinoblastoma Rb (Weinberg et al., 1992) and the gene encoding p130 linked with Rb (Rbr-2) (Hannon et al., 1993, Genes and Development, 7, 2378–2391) are also very highly activated in the p21 transfectants of the U937 cells (cf. FIG. 1). The expression of the p53 gene at the mRNA and protein level remains undetectable both in the control and in the transfected cells (results not shown). The expression of the Rb gene establishes its tumor suppressor properties, as it does for the Rbr-2 gene for its involvement in the cell cycle and the chromosomal location of HUMSIAH. However, the analysis of the cell cycle by FACS (flow cytometric analysis) in three independent experiments (using popidium iodide) did not reveal a significant difference between the control transfected U937 cells and the p21-WAF1 U937 cells (example of results obtained: i) control transfected U937 cells: in $G_1$ 65%/S 29%/$G_2$ 6%; ii) p21-WAF1 U937 cells: $G_1$ 64%/S 30%/$G_2$ 6%).

The doubling time is also similar with the two lines, respectively 33 hours for the control transfected U937 cells and 36 hours for the p21-WAF1 U937 cells.

Figure 2:
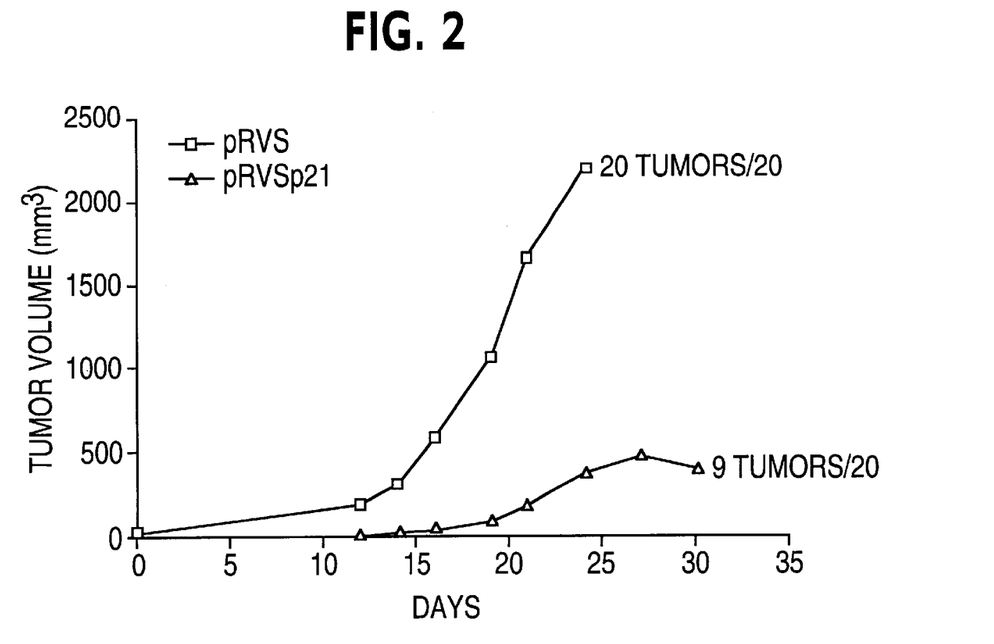
FIG. 2: Tumorigenicity of the control pRSV U937 cells transfected with the vector alone compared with the transfected pRSV-p21 cells. The tumorigenicity is evaluated after subcutaneous injection of $10^7$ cells into scid/scid mice.

The injection into Scid/Scid mice is carried out as described above. The comparison is made with cells transfected with the vector alone (pRSV). GAPDH is used as control. After transfection of the cells U937 with the preceding vectors, it is observed that the U937 cells stably transfected with p21WAF1 (pRSV-p21) show a significant disappearance of the malignant phenotype (cf. FIG. 2). After 24 days, the scid/scid mice injected with U937 cells containing the vector alone have tumors in all the sites and having a volume such that they had to be sacrificed. By contrast, only 9 sites out of 20 sites of injection of transfected p21WAF1 U937 cells formed apparently delayed tumors and much smaller in volume. No other tumor appeared after 6 additional weeks of observation. Thus, the specific induction of the expression of the p21-WAF1 gene, without substantial variation in the cell cycle, is partly responsible for the activation of the molecular process of tumor suppression.

EXAMPLE 2

DNase I Method—Influence of p21WAF1 on the Reorganization of the Nucleus

The objective of this example is to study the role of p21WAF1 in a possible reorganization of the nucleus.

The method used for this determination, because of the fact that the position of the chromosomes in the nucleus could have an influence on the cell phenotype, is the so-called DNase I method which makes it possible to visualize the exposed DNA, that is to say portions of chromosome which are more sensitive to DNase I under certain conditions, which makes it possible to label them.

To do this, the DNase I method as described in U.S. Pat. No. 5,264,343 is used but in a manner which allows it to be applied to tissues.

The tissues are fixed in a 4% mixture of paraformaldehyde in PBS for 10 minutes, dehydrated and stored at −80° C.

The labeling by "nick translation" is carried out using a "nick-translation" buffer (NTB) and a 10×solution (100 ml).

NTB comprises 50 mM Tris-HCl, pH 8, 5 mMgCl$_2$, 10 mM β-mercaptoethanol and 50 ng/ml BSA. The 10×solution (100 ml) contains 50 ml of Tris-HCl, pH 8 (1 M), 3.3 ml of MgCl$_2$ (1.5 M), 700 ml of β-mercaptoethanol (14.2 m) and 1.66 µL of BSA (at 3%).

The tissues are treated with 100 µl of NTB containing 30 U of DNase I for each section. The medium is incubated for 3 minutes at room temperature, blocked with 20 mM EDTA, pH 8, for 3 minutes, and then washed 3 times with NTB.

100 µl of NTB are then used with 40 U of DNA polymerase I and 100 µM dNTP digoxigenin (10% 10×solution for each section). The medium is incubated for 6 minutes at room temperature and blocked with EDTA as above, and washed 3 times with NTB.

The labeling is carried out after saturation with 3% BSA, revealing with anti-DIG antibodies labeled with peroxidase, after washing 3 times for 3 minutes with PBS, thyramide-TRITC is used as substrate and then washed 3 times for 3 minutes with PBS.

The plates are then counterstained with chromomycin 3-A.

The analysis is carried out by cofocal laser microscopy (MRC 600 Bio-rad) in fluorescent mode (the results are represented by colored photographs not included in the present description).

The parental U937 cancer cells or the same cells transfected with the control vector exhibit a diffuse appearance as observed in biopsies of mammary carcinomas. The U937 cells transfected with p21WAF1 exhibit a radical change in the exposure of the genome to DNase I by exhibiting an appearance which is similar to that of the US3–US4 cells having a tumor phenotype suppression, just as they exhibit an appearance corresponding to that of epithelial cells observed on biopsies of normal breasts, that is to say a labeling according to a crown at the periphery of the nucleus.

This reorganization of nuclei may be associated with the activation of genes in the suppression of tumorigenicity. This reorganization of the nucleus, induced by p21-WAF1, could either be a direct effect of this induction or linked to its function as inhibitor of cdk ("Cyclin-dependent kinase") activity. The group of nuclear lamins (Foisnier et al., 1993, Cell., 73, 1267–1279) is one of the targets characterized for the mitotic cdk activity. The nuclear modifications may result from a change in the state of phosphorylation of these nuclear lamins. The origin of this substantial change in the distribution of the sites sensitive to DNase I could therefore be the triggering of the movement of chromosomes inside the nucleus induced by p21-WAF1.

EXAMPLE 3

Labeling in situ

Hybridization of the DNA in situ is carried out with an alphoid centromeric probe 16, as described above (Klinger K. et al. Am. J. Hum. Genet. 51, 55–65 (1992)).

Figure 3:
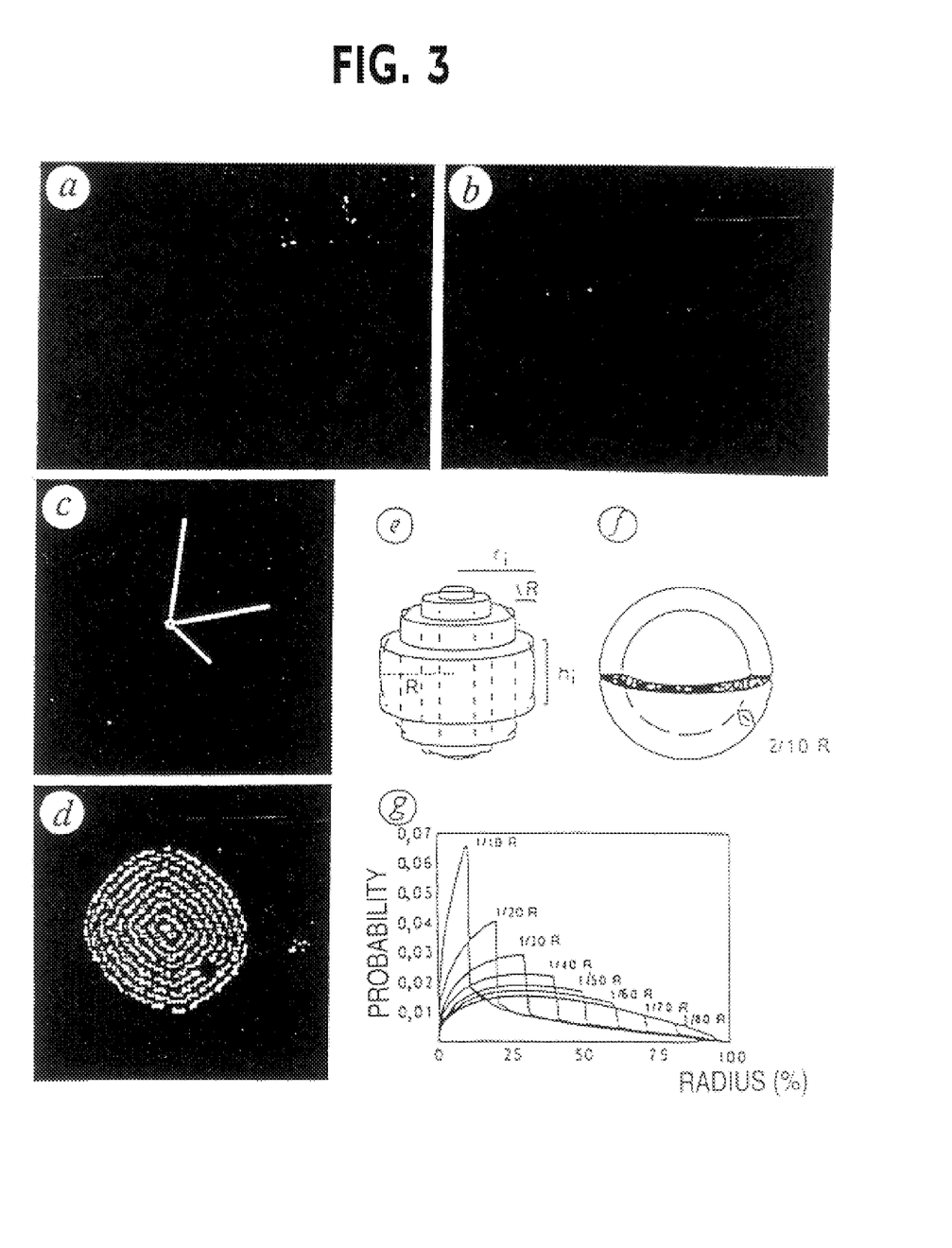

HUMSIAH and Rb-2 being colocated on chromosome 16q, while Rb is located on chromosome 13q, corresponding probes are used. By using fluorescence in situ hybridization (FISH), combined with digital optomicroscopy, with these alphoid centromeric probes corresponding to chromosome 16, it is possible to observe on the colored photographs obtained (in black and white in the present description) (cf. FIG. 3, a)–d)) that the U937 cells exhibit a hybridization signal near the center of the nucleus. By contrast, the U937 cells transfected with p21WAF1 or the US3–US4 cells having a tumor suppression exhibit a signal which is detected in the peripheral region of the nucleus. The nucleus of the control U937 transfected cells and the p21-WAF1 transfected cells are labeled with DAPI (blue). The FISH signal is revealed with tyramide-TRITC (red). From a physiological point of view, these observations confirm the evidence for a chromosomal territorial organization at the interphase. The precise topological conformation of the gene in the nucleus has an obvious functional repercussion. In particular, this reorganization of the nucleus could be responsible for the activation of the genes involved in the suppression of tumors, which are silent in tumor processes.

For each probe used, the distance from the border of the nucleus was measured and integrated in a model (cf. FIG. 3, e)–g)).

Figure 4:
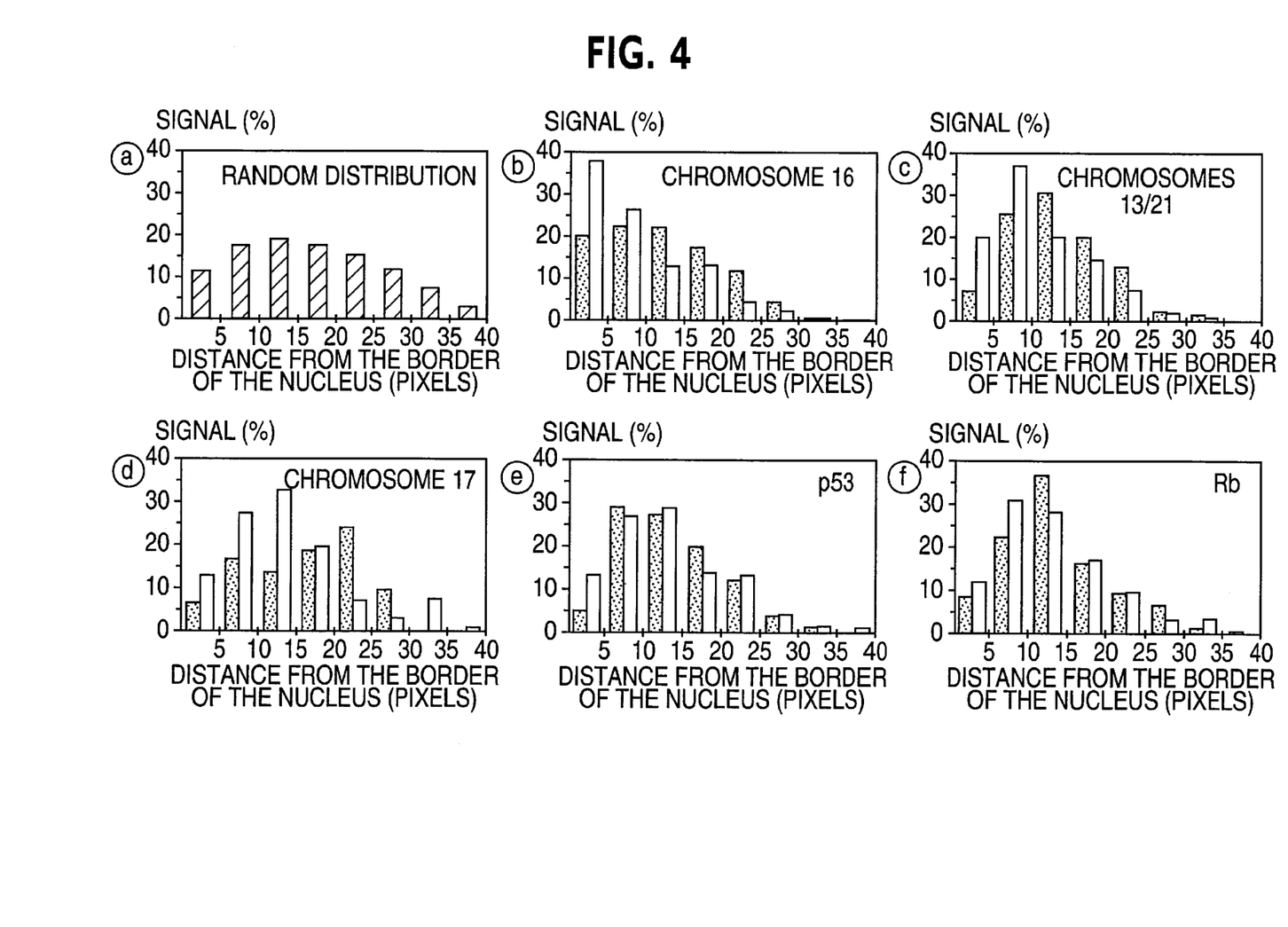
FIG. 4: Histogram of the distribution of the signals as measured from the extreme border of the nucleus. Comparison between the pRSV U937 control transfected cells (■) and the pRSV-p21 U937 transfected cells (□).

It was found that the p21-WAF1 U937 transfected cells exhibit an overall redistribution of the signals with a net shift toward the peripheral region of the nucleus (cf. FIG. 4). The distribution of these FISH signals corresponding to the centromeric probes is, statistically, different between the tumor cells and those exhibiting a tumor suppression. The $\chi^2$ test is very significant (p<0.001). By using the probes specific for the Rb and p53 genes, no significant statistical difference is observed in the distribution between the FISH spots corresponding to the cells transfected with the pRSV vector alone and with p21-WAF1 (using the $\chi^2$ test) (cf. FIG. 4). From the physiological point of view, these observations are complementary to the observations strongly suggesting the territorial chromosomal organization at the interphase (Manuelidis et al., 1990, Science, 250, 1533–1540; Cremer et al., 1993, Cold Spring Harbor Symposia on Quantitative Biology, LVIII, 777–792, and Puck et al., 1991). Specific domains of chromatin distinctly and nonrandomly occupy spatial positions as described above (Hulspas et al., 1994, Chromosoma, 103, 286–292; Nagele et al., 1995, Science, 270, 1831–1835). It is not certain that a correlation exists between the expression of the gene and the repositioning of the chromosome, this remains to be explored since some results indicate both active and inactive genes preferably located in the peripheral territories of the chromosomes. Our study shows that in the case of a suppression of tumorigenicity induced by p21-WAF1, the centromeric regions, not containing coding genetic material, are repositioned. This repositioning of the centromeric regions of the chromosomes analyzed above may be responsible for a mechanism by which the architecture of the chromosomal territory is modified. Such territorial modifications may influence the spatial environment of the specific gene and modulate their expression. Obviously, the precise topological conformation of the genes inside the nucleus ought to have functional repercussions. Indeed, recent studies describing the diversity of the effects of position in Drosophila have clearly demonstrated the functional importance of the specific nuclear architecture in the expression of genes (Csink et al., 1996, Nature, 381, 529–531; Dernburg et al., 1996, 85, 745–749).

In conclusion, using both model systems for analyzing the suppression of tumorigenicity and stable transfection, the results presented below show that p21-WAF1 induces the repositioning of the genetic material in the nucleus, associated with potentially important functions for achieving tumor suppression. These results show the central role played by p21WAF1 in the organization of the nucleus, in the positioning of the chromosomes and in the activation of the process of suppression of tumorigenicity.

What is claimed is:

1. A method for determining the state of one or more malignant cells comprising the steps of:
   (a) fixing the cells by the formalin method using 4% neutral buffered paraformaldehyde,
   (b) labeling at least one centromeric gene within the nucleus of said cell by fluorescence in situ hybridization using centromeric probes,
   (c) determining the position of said labeled centromeric gene from the border of the nucleus, and
   (d) evaluating the deviation of said position compared with the position of the same probed centromeric gene in a normal cell as an index of its state of malignancy,
wherein the normal cell corresponds to a peripheral location of the chromosome carrying said centromeric probe.

2. The method according to claim 1, wherein the conformation of said gene is evaluated by fluorescence in-situ hybridization,
   wherein centromeric probes are used as hybridization probes; wherein the normal cell is defined as a cell having a centromere at a peripheral location of a chromosome carrying said gene, and
   wherein the chromosome is chromosome 13q and/or 16q.

3. The method according to claim 1, wherein the state of the malignant cell is determined, and then said cell is treated with an anti-cancer product or a product acting in a pathology not directly linked to oncogenesis and the activity of said anti-cancer or said related product is evaluated by measuring the variation in the malignancy index.

* * * * *

SEQUENCE LISTING

<160> NUMBER OF SEQ ID NOS: 2

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: PCR Primer

<400> SEQUENCE: 1
tgggacagct accgcagcat gagcga                                        26

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: PCR Primer

<400> SEQUENCE: 2
cacagtacag ggctgtcgcc gctgtt                                        26